US007854229B2

(12) United States Patent
Sadir et al.

(10) Patent No.: US 7,854,229 B2
(45) Date of Patent: Dec. 21, 2010

(54) CRADLE OR BED WITH ISOLATION FROM ROOM CONTAMINATION, WITH CONTROLLED TEMPERATURE AND MOISTURE

(75) Inventors: Raul Isaac Sadir, São Paulo (BR); José Maria Rodriguez Perez, São Paulo (BR)

(73) Assignee: Vecoflow Ltda., Sao Paulo (BR)

(*) Notice: Subject to any disclaimer, the term of this patent is extended or adjusted under 35 U.S.C. 154(b) by 296 days.

(21) Appl. No.: 11/324,632

(22) Filed: Jan. 4, 2006

(65) Prior Publication Data

US 2007/0151564 A1 Jul. 5, 2007

(51) Int. Cl.
*A61G 10/00* (2006.01)
*A61M 15/00* (2006.01)
*A01K 31/20* (2006.01)
*E06B 7/02* (2006.01)
*F27D 11/00* (2006.01)

(52) U.S. Cl. ............................ 128/205.26; 128/202.12; 128/202.13; 237/3; 237/14; 237/15; 454/195; 219/385; 219/386; 219/400

(58) Field of Classification Search ............ 128/205.26, 128/202.12, 202.13; 237/3, 14, 15; 454/195; 219/385, 386, 400
See application file for complete search history.

(56) References Cited

U.S. PATENT DOCUMENTS 5,759,149 A * 6/1998 Goldberg et al. .............. 600/22
6,013,119 A * 1/2000 Cecchi et al. .............. 55/385.2
6,711,937 B2 * 3/2004 Richards et al. ............ 73/29.01

* cited by examiner

*Primary Examiner*—Patricia M Bianco
*Assistant Examiner*—Nihir Patel
(74) *Attorney, Agent, or Firm*—Gottlieb, Rackman & Reisman, P.C.

(57) ABSTRACT

New bed or a new cradle model to be used specifically in hospitals, clinics and similar facilities for babies, which presents a specific laminar air flow system, with controlled temperature and moisture, for the patient desired levels, which provides reduction of the contamination on the micro environment where it is placed, allowing its use by patients under critical and delicate condition, with easy access to the patients.

2 Claims, 1 Drawing Sheet

CRADLE OR BED WITH ISOLATION FROM ROOM CONTAMINATION, WITH CONTROLLED TEMPERATURE AND MOISTURE

BACKGROUND OF THE INVENTION

This report presents the detailed description and is accompanied by a explanatory drawing of a new bed or a new cradle model to be used specifically in hospitals, clinics and similar facilities for babies, model which presents a specific laminar air flow system, with controlled temperature and moisture, for the patient desired levels, which provides reduction of the contamination on the micro environment where it is placed, allowing its use by patients under critical and delicate condition, with easy access to the patients.

In the existing current equipment the patient isolation from room contamination either is not available or that isolation is performed by mechanical barriers that make the access difficult for patient care providers. The most known current equipment consists of incubators and the heated cradle by radiant heating.

Incubators are closed equipment with controlled heating and a complete reverse ambient isolation, making the access difficult to the physician and/or the nurses and many times the access to the patient is done through the equipment openings which limit the patient handling.

The radiant heating cradles have the controlled temperature performed by thermal irradiation, which may cause an overlooked higher liquid loss in the patient, which might present harmful effect to the patient condition, increasing the need for specific and more rigorous care. In addition, that cradle model does not have isolation from room contamination.

Hence, on the grounds of the factors hereinbefore mentioned for the current equipment and with the purpose to overcome these issues, the cradle or bed with isolation of the room contamination, with controlled temperature and moisture, object of the present patent has been conceived, developed and substantiated, and comes to fulfill the need in the area of infant critical patient care, presenting an open bed with easy access for the physician and/or nurses to the patient, providing the necessary isolation from room contamination and controlled temperature and moisture, with the required levels for each patient supported by this equipment.

BRIEF DESCRIPTION OF THE DRAWING

Following are references to the illustrative drawing that accompanies this descriptive report. In order to better understand and to illustrate this report, it can be seen that:

The drawing shows a schematic view of the cradle or bed with isolation from room contamination, with controlled temperature and moisture, object of the present patent with all of its configuration details.

DETAILED DESCRIPTION OF THE INVENTION

Figure 1:
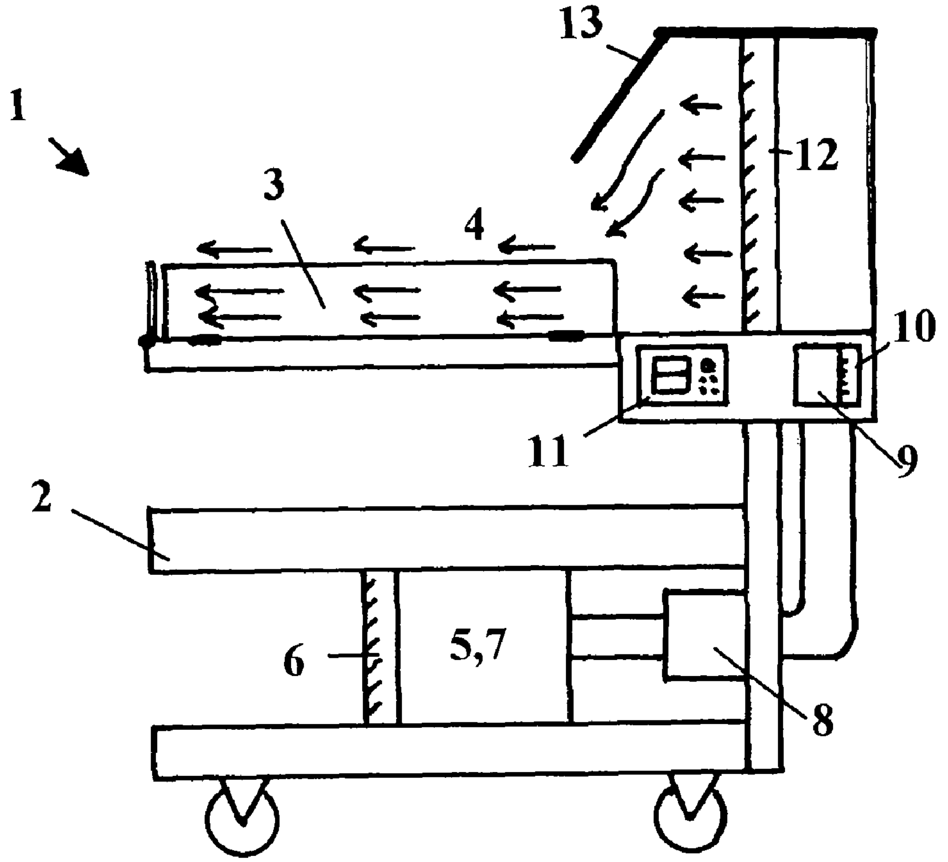

The bed or cradle with isolation from room contamination and with controlled temperature and moisture (1) object of the present patent refers to a mobile structure (2) with an open bed (3), where there is a laminar air flow with controlled temperature and moisture throughout its length (4), providing isolation from room contamination and easy access to the patient. Where the laminar air flow (4) is generated by a motor (5) that suctions the room air through a bacteriological filter (6) responsible for retaining the coarse airborne particulate material, and either may pass through an activated charcoal filter (7) or not, following into a convection heater (8) preferably by electrical resistors and then passing through a specific humidifier (9) with water level control (10) or vice versa. Where the heater (8) and the humidifier (9) have a servo controller (11), allowing the regulation and maintaining the temperature and moisture levels required for each case. Finally, the air flow passes through a HEPA filter (12) responsible for the airborne submicron particulate material retention, and the air is directed through a specific hinged device, controlling and directing the air flow (13), controlling the air flow velocity in order to create a laminar unidirectional and horizontal flow, without turbulence over the bed throughout its length, maintaining a barrier that keeps a suitable micro environment for the patients and providing isolation from room contamination, and controlled temperature and moisture, with easy access to the patient.

Therefore, by the configuration and operational characteristics described hereinbefore, it is possible to clearly note that the "CRADLE OR BED WITH ISOLATION FROM ROOM CONTAMINATION, WITH CONTROLLED TEMPERATURE AND MOISTURE" here proposed, refers to a new State of the Art equipment, which comes to fulfill the needs in its area, in a novelty way facilitating and improving the care conditions for infant patients which require critical care, and so deserving the Privilege for a Utility Model Patent.

What is claimed is:

1. A cradle for use with babies in hospitals, clinics and similar facilities, said cradle operating to isolate a baby from room contamination while providing a controlled temperature and moisture environment, said cradle comprising:

- a mobile structure with an unenclosed bed, having an upper surface open to the environment and
- a laminar air flow device for providing a controlled temperature and moisture throughout a length of said bed, said laminar air flow device comprising:
  - a motor which suctions environmental room air through a bacteriological filter;
  - an activated charcoal filter coupled to said bacteriological filter;
  - a convection heater coupled to said activated charcoal filter;
  - a humidifier having a water level control coupled to said convection heater, said convection heater and said humidifier having a servo controller,
  - a HEPA filter coupled to said humidifier, said filter being positioned proximate an end of said bed; and
- a hinged device, positioned in a flow path of air exiting said REPA filter for controlling and directing a flow of said air and controlling a velocity of said flow of air in order to create a laminar, unidirectional and horizontal flow of air, without turbulence, over said upper surface of said unenclosed bed throughout a length thereof.

2. A cradle for use with babies in hospitals, clinics and similar facilities, said cradle operating to isolate a baby from room contamination, while providing a controlled temperature and moisture environment, said cradle comprising:

- a mobile structure having an unenclosed bed, having an upper surface open to the environment, and
- a laminar air flow device for providing a controlled temperature and moisture throughout a length of said bed, said laminar air flow device comprising:
  - a motor which suctions environmental room air through a bacteriological filter;
  - a convection heater coupled to said bacteriological filter;
  - a humidifier, having a water level control, coupled to said convection heater, said convection heater and said humidifier, having a servo controller,
  - a HEPA filter coupled to said humidifier, said filter being positioned proximate an end of said bed; and a hinged device, positioned in a flow path of air exiting said REPA filter for controlling and directing a flow of said air and controlling a velocity of said flow of air in order to create a laminar, unidirectional and horizontal flow of air, without turbulence, over said unenclosed bed throughout a length thereof.

* * * * *